US006214596B1

(12) United States Patent
Asgharian et al.

(10) Patent No.: US 6,214,596 B1
(45) Date of Patent: Apr. 10, 2001

(54) LIQUID ENZYME COMPOSITIONS AND METHODS OF USE IN CONTACT LENS CLEANING AND DISINFECTING SYSTEMS

(75) Inventors: Bahram Asgharian; Bor-Shyue Hong, both of Arlington, TX (US)

(73) Assignee: Alcon Laboratories, Inc., Fort Worth, TX (US); .

(*) Notice: Subject to any disclaimer, the term of this patent is extended or adjusted under 35 U.S.C. 154(b) by 0 days.

(21) Appl. No.: 09/144,674

(22) Filed: Sep. 1, 1998

Related U.S. Application Data

(63) Continuation-in-part of application No. 08/769,256, filed on Dec. 18, 1996, now Pat. No. 6,069,120.

(51) Int. Cl.[7] .............................. C12N 9/96; C11D 3/386
(52) U.S. Cl. ........................... 435/188; 510/114; 510/395
(58) Field of Search ............................ 435/188; 510/114, 510/393

(56) References Cited

U.S. PATENT DOCUMENTS

| | | | |
|---|---|---|---|
| Re. 32,672 | 5/1988 | Huth et al. | 435/264 |
| 3,873,696 | 3/1975 | Randeri et al. | 424/680 |
| 3,910,296 | 10/1975 | Karageozian et al. | 134/2 |
| 3,931,319 | 1/1976 | Green et al. | 564/286 |
| 4,026,945 | 5/1977 | Green et al. | 526/294 |
| 4,318,818 | 3/1982 | Letten et al. | 510/393 |
| 4,407,791 | 10/1983 | Stark | 424/78.04 |
| 4,414,127 | 11/1983 | Fu | 510/115 |
| 4,462,922 | 7/1984 | Boskamp | 510/393 |
| 4,525,346 | 6/1985 | Stark | 424/78.04 |
| 4,537,706 | 8/1985 | Severson | 510/393 |
| 4,614,549 | 9/1986 | Ogunbiyi et al. | 134/19 |
| 4,615,882 | 10/1986 | Stockel | 424/78.04 |
| 4,717,662 | 1/1988 | Montgomery et al. | 435/99 |
| 4,758,595 | 7/1988 | Ogunbiyi et al. | 424/78.26 |
| 4,836,986 | 6/1989 | Ogunbiyi et al. | 422/28 |
| 5,039,446 | 8/1991 | Estell | 510/321 |
| 5,089,163 | 2/1992 | Aronson et al. | 510/393 |
| 5,096,607 | 3/1992 | Mowrey-McKee et al. | 422/28 |
| 5,281,277 | 1/1994 | Nakagawa et al. | 134/18 |
| 5,314,823 | 5/1994 | Nakagawa | 435/264 |
| 5,503,766 | 4/1996 | Kulperger | 510/383 |
| 5,604,190 | 2/1997 | Chowhan et al. | 510/114 |
| 5,605,661 | 2/1997 | Asgharian et al. | 422/28 |
| 5,785,767 | 7/1998 | Kimura et al. | 134/42 |
| 5,820,696 | 10/1998 | Kimura et al. | 134/42 |

FOREIGN PATENT DOCUMENTS

| | | |
|---|---|---|
| 1 150 907 | 8/1983 | (CA) . |
| 0 456 467 | 11/1991 | (EP) . |
| 57-24526 | 5/1982 | (JP) . |
| 92-180515 | 7/1989 | (JP) . |
| 4-93919 | 3/1992 | (JP) . |
| 92-143718 | 5/1992 | (JP) . |
| 4-243215 | 8/1992 | (JP) . |
| 4-370197 | 12/1992 | (JP) . |
| WO 95/12655 | 5/1995 | (WO) . |

OTHER PUBLICATIONS

Novo Nordish, RD 353,036, Sep. 1993.*

Crossin, M. C., "Protease Stabilization by Carboxylic Acid Salts: Relative Efficiencies and Mechanisms", *Journal of the American Oil Chemists,* vol. 66, No. 7, pp. 1010–1014 (1989).

Delgado, "Solubility behavior of enzymes after addition of polyethylene glycol to erthrocyte hemolysates", *Biotechnology And Applied Biochemistry,* vo. 10, No. 3, pp. 251–256 (1988).

Fuke, I., et al., "Synthesis of poly (ethylene glycol) derivataives with different branchings and their use for protein modification", *Journal of Controlled Release,* vol. 30, pp. 27–34 (1994).

Lo, J.; Silverman, H.; and Korb, D.; "Studies on cleaning solutions for contact lenses", *Journal of the American Optometric Association,* vol. 40, pp. 1106–1109 (1969).

"Pancreatin", *United States Pharmacopeia,* pp. 1149–1151 (1995).

Royer, "Peptide Synthesis in Water and the Use of Immobilized Carboxypeptidase Y for Deprotection", *Journal of the American Chemical Society,* vol. 101, pp. 3394–3396 (1979).

Segal, et al., "The interaction of alkynyl carboxylates with serine enzymes", *FEBS Letters,* vol. 247, No. 2, pp. 217–220 (1989).

* cited by examiner

*Primary Examiner*—Jon P. Weber
(74) *Attorney, Agent, or Firm*—Michael C. Mayo; Gregg C. Brown

(57) ABSTRACT

Stable liquid enzyme compositions containing an ophthalmically acceptable enzyme and methods involving the combined use of these compositions with an antimicrobial agent are disclosed for the simultaneous cleaning and disinfecting of contact lens. Methods for a daily use regimen are also disclosed.

38 Claims, 1 Drawing Sheet

Comparison of the Stability of a Present Invention Composition (Comp. 1) with Other Compositions at 40° C

LIQUID ENZYME COMPOSITIONS AND METHODS OF USE IN CONTACT LENS CLEANING AND DISINFECTING SYSTEMS

This application is a continuation-in-part of patent application Ser. No. 08/769,256, filed Dec. 18, 1996 now U.S. Pat. No. 6,069,120, which claims priority to U.S. patent application Ser. No. 08/516,664, filed Aug. 18, 1995 (now U.S. Pat. No. 5,605,661).

BACKGROUND OF THE INVENTION

The present invention relates to the field of contact lens cleaning and disinfecting. In particular, this invention relates to liquid enzyme compositions and methods for cleaning human-worn contact lenses with those compositions. The invention also relates to methods of simultaneously cleaning and disinfecting contact lenses by combining the liquid enzyme compositions of the present invention with a chemical disinfecting agent.

Various compositions and methods for cleaning contact lenses have been described in the patent and scientific literature. Some of these methods have employed compositions containing surfactants or enzymes to facilitate the cleaning of lenses. The first discussion of the use of proteolytic enzymes to clean contact lenses was in an article by Lo, et al. in the *Journal of The American Optometric Association,* volume 40, pages 1106–1109 (1969). Methods of removing protein deposits from contact lenses by means of proteolytic enzymes have been described in many publications since the initial article by Lo, et al., including U.S. Pat. No. 3,910,296 (Karageozian, et al.).

Numerous compositions and methods for disinfecting contact lenses have also been described. Those methods may be generally characterized as involving the use of heat and/or chemical agents. Representative chemical agents for this purpose include organic antimicrobials such as benzalkonium chloride and chlorhexidine, and inorganic antimicrobials such as hydrogen peroxide and peroxide-generating compounds. U.S. Pat. Nos. 4,407,791 and 4,525,346 (Stark) describe the use of polymeric quaternary ammonium compounds to disinfect contact lenses and to preserve contact lens care products. U.S. Pat. Nos. 4,758,595 and 4,836,986 (Ogunbiyi) describe the use of polymeric biguanides for the same purpose.

Various methods for cleaning and disinfecting contact lenses at the same time have been proposed. Methods involving the combined use of proteolytic enzymes and peroxides to clean and disinfect contact lenses simultaneously, are described in U.S. Pat. No. Re 32,672 (Huth, et al.). A representative method of simultaneously cleaning and disinfecting contact lenses involving the use of proteolytic enzymes and quaternary ammonium compounds is described in Japanese Patent Publication 57-24526 (Boghosian, et al.). The combined use of a biguanide (i.e., chlorhexidine) and liquid enzyme compositions to simultaneously clean and disinfect contact lenses is described in Canadian Patent No. 1,150,907 (Ludwig, et al.). Methods involving the combined use of dissolved proteolytic enzymes to clean and heat to disinfect are described in U.S. Pat. No. 4,614,549 (Ogunbiyi). The combined use of proteolytic enzymes and polymeric biguanides or polymeric quaternary ammonium compounds is described in copending, commonly assigned U.S. patent application Ser. No. 08/156,043 and in corresponding European Patent Application Publication No. 0 456 467 A2 (Rosenthal, et al.), as well as in U.S. Pat. No. 5,096,607 (Mowrey-McKee, et al.).

The commercial viability of most prior enzymatic cleaning products has depended on the use of stable enzyme tablets. More specifically, the use of solid enzymatic cleaning compositions has been necessary to ensure stability of the enzymes prior to use. In order to use such compositions, a separate packet containing a tablet must be opened, the tablet must be placed in a separate vial containing a solution, and the tablet must be dissolved in order to release the enzyme into the solution. This practice is usually performed only once a week due to the cumbersome and tedious procedure and potential for irritation and toxicity. Moreover, the enzymatic cleaning tablets contain a large amount of excipients, such as effervescent agents (e.g., bicarbonate) and bulking agents (e.g., sodium chloride). As explained below, such excipients can adversely affect both cleaning and disinfection of the contact lenses.

There have been prior attempts to use liquid enzyme compositions to clean contact lenses. However, those attempts have been hampered by the fact that aqueous liquid enzyme compositions are inherently unstable. When a proteolytic enzyme is placed in an aqueous solution for an extended period (i.e., several months or more), the enzyme may lose all or a substantial portion of its proteolytic activity. Steps can be taken to stabilize the compositions, but the use of stabilizing agents may have an adverse effect on the activity of the enzyme. For example, stabilizing agents can protect enzymes from chemical instability problems during storage in an aqueous liquid, by placing the enzymes in a dormant physical conformation. In addition to the general problems referred to above, a commercially viable liquid enzyme preparation for treating contact lenses must be relatively nontoxic, and must be compatible with other chemical agents used in treating contact lenses, particularly antimicrobial agents utilized to disinfect the lenses.

The following patents may be referred to for further background concerning prior attempts to stabilize liquid enzyme formulations: U.S. Pat. Nos. 4,462,922 (Boskamp); 4,537,706 (Severson); and 5,089,163 (Aronson). These patents describe detergent compositions containing enzymes. The detergent compositions may be used to treat laundry, as well as other industrial uses. Such detergents are not appropriate for treating contact lenses. The compositions of the present invention do not contain a detergent, or other agents potentially damaging or irritating to the eye.

U.S. Pat. No. 5,281,277 (Nakagawa) and Japanese Kokai Patent Applications Nos. 92-370197; 92-143718; and 92-243215 describe liquid enzyme compositions for treating contact lenses. The compositions of the present invention are believed to provide significant improvements relative to the compositions described in those publications.

Commonly assigned U.S. Pat. Nos. 5,604,190 (Chowhan et al.) and 5,605,661 (Asgharian et al.) are directed to liquid enzyme compositions. U.S. Patent No. 5,605,661 is directed to liquid compositions containing 30–70% weight/volume of "mixed polyols," i.e., a monomeric polyol and polymeric polyol, to stabilize enzymes in the liquid concentrate. The present invention is directed to mixed polyol compositions which provide a significantly improved stability profile over the prior art compositions.

SUMMARY OF THE INVENTION

Figure 1:
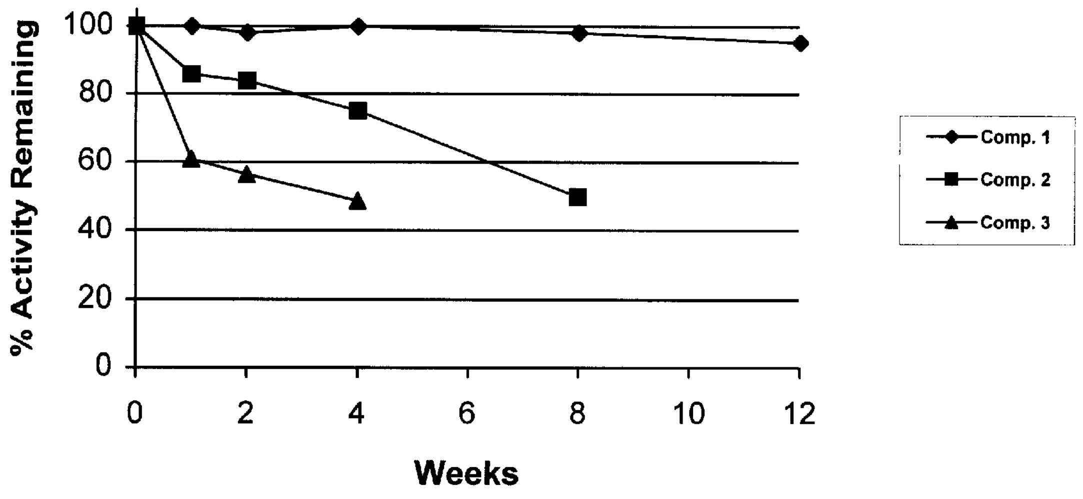
FIG. 1 is a graph comparing the proteolytic stability of a liquid enzyme composition of the present invention with other compositions, at 40° C. through 12 weeks.

The present invention is directed to liquid enzyme compositions possessing improved enzyme stabilizing efficacy.

The liquid enzyme compositions of the present invention contain critical amounts of selected stabilizing agents. The stabilizing agents utilized are calcium ion, a monomeric polyol, a polymeric polyol and a borate/boric acid compound. The amounts of stabilizing agents utilized have been delicately balanced, such that maximum stability is achieved, while maximum activity is later obtained when the composition is put into use. A suitable preservative may also be added to the liquid enzyme compositions of the present invention to preserve the liquid enzyme compositions from microbial contamination when the compositions are packaged in multiple use containers.

The present invention also provides methods for cleaning contact lenses with the above-described liquid enzyme compositions. In order to clean a soiled lens, the lens is placed in a few milliliters of an aqueous solution and a small amount, generally one to two drops, of the enzyme composition is added to the solution. The lens is then soaked in the resultant cleaning solution for a time sufficient to clean the lens.

The liquid enzyme compositions of the present invention are preferably combined with an aqueous disinfecting solution to simultaneously clean and disinfect contact lenses. The compositions and methods of the present invention provide greater ease of use. This ease of use enables contact lens users to clean their lenses 2 to 3 times a week, or more preferably, every day. It has been found that daily use of the liquid enzyme compositions of the present invention results in dramatically better cleaning and safety, as compared to the once-a-week enzyme cleaning regimens currently being utilized.

The enzyme compositions of the present invention are formulated as concentrated, multi-dose liquids, which provide a significantly improved enzyme stability profile. This improved stability allows the liquid compositions to have greater shelf life and the option of being commercially transported without refrigeration.

DETAILED DESCRIPTION OF THE INVENTION

It has been discovered that liquid enzyme compositions containing a particular combination of ingredients, and in particular concentration ranges, provides a significantly improved enzyme stability profile over prior liquid enzyme compositions. The liquid enzyme compositions of the present invention are comprised of an enzyme, stabilizing agents and water. The stabilizing agents required by the present invention are a monomeric polyol, a polymeric polyol, calcium ion and a borate/boric acid compound.

As used herein, the term "monomeric polyol" refers to a compound with 2 to 6 carbon atoms and at least two hydroxy groups. Examples of monomeric polyols are glycerol, propylene glycol, ethylene glycol, sorbitol and mannitol. Preferably, the monomeric polyols are selected from polyols having 2–3 carbons and at least two hydroxy groups ("2–3 carbon polyol"). Examples of 2–3 carbon polyols are glycerol, 1,2-propane diol ("propylene glycol"), 1,3-propane diol and ethylene glycol. Glycerol and propylene glycol are the most preferred 2–3 carbon polyols.

As used herein, the term "polymeric polyol" refers to a polyalkoxylated glycol with a molecular weight ranging from 200–600. Examples of polymeric polyols are polyethylene glycol 200 (denoting a molecular weight of 200, "PEG 200") and PEG 400. The PEGs may optionally be monoalkoxylated. Examples of monoalkoxylated PEGs are monomethoxy PEG 200 and ethoxy PEG 400. Though these alkoxylated PEGs are not technically polyols, they are similar in structure to the non-alkoxylated PEGs; therefore, for defining purposes, they are included in the term "polymeric polyol."

The monomeric and polymeric polyol amounts will vary depending on the particular combination of polyols used. In general, liquid enzyme compositions of the present invention will require 40 to 85% weight/volume ("% w/v") of a polyol mixture to achieve the necessary criteria for efficacious and commercially viable liquid enzyme compositions, as described above. The ratio of monomeric to polymeric polyols is also important. In general, the monomeric polyol:polymeric polyol ratio will be from 1:5 to 5:1, with a preferred ratio being 2:1 to 1:2, weight:weight. While any of the polyols can be components of the compositions of the present invention, particular polyols may be used depending on the particular intended use. For example, propylene glycol, which has preservative activity, is a preferred monomeric polyol when the need for an additional preservative present in a liquid enzyme composition of the present invention is desired. The most preferred combination of polyols used in the compositions of the present invention are glycerol and PEG-400. The most preferred amount of the glycerol/PEG-400 combination is 25% w/v glycerol with 50% w/v PEG-400.

The liquid enzyme compositions of the present invention will also contain an effective amount of calcium ion. The calcium ion contained in the compositions of the present invention may be obtained by the addition of various calcium salts. For example, the calcium ion source may be obtained from calcium chloride, calcium acetate and calcium ascorbate or other water soluble salts of calcium. The most preferred calcium ion source is calcium chloride. As used herein, "effective amount of calcium ion" refers to that amount of calcium ion which enhances the proteolytic stability of an enzyme in the liquid enzyme compositions of the present invention. While that amount will vary depending upon the various components present, typical calcium ion concentrations will be about 1 to 90 millimolar. Preferred concentrations will be about 4.5 to 45 millimolar, and most preferred concentrations will be of from 10 to 25 millimolar.

The compositions of the present invention will also contain an effective amount of a borate/boric acid compound. As used herein, "borate/boric acid compound" refers to an inorganic compound comprising boron and one or more oxygen groups, and which is either in acid or base form when dissolved in a composition of the present invention. Sources of borate/boric acid compounds include alkali metal salts of borate, boric acid and borax. As used herein, "effective amount of a borate/boric acid compound" refers to that amount of a borate/boric acid compound contained in a liquid enzyme composition of the present invention which enhances the proteolytic stability of the enzyme. While such an amount will vary depending on other components present in the concentrate, the amount will be about 0.3 to 8.0% (w/v). Preferred amounts will be of from 0.5 to 1.5% (w/v). The borate/boric acid compound may also contribute to the anti-microbial preservation of the liquid enzyme compositions of the present invention to a level effective for multi-use dispensing. The solubility of the borate/boric acid compound may be limited in water. The solubility of these compounds, however, may be increased by increasing the amount of polyol employed.

A variety of preservatives may be employed to preserve liquid enzyme compositions of the present invention intended for multi-dispensing. In general, any of the disinfecting agents listed below for use in the disinfecting solutions of the methods of the present invention, with the exception of oxidative disinfecting agents, may be used. Particularly preferred, are the polymeric quaternary ammonium compounds, the most preferred is polyquaternium-1. The amount of preservative used will depend on several factors including the anti-microbial efficacy of the particular agent and any synergistic interaction the agent may have with the liquid enzyme composition. In general, 0.0001 to 0.1% w/v of the preservative agent will be used.

The compositions of the present invention may optionally contain a reversible enzyme inhibitor. The inhibitor will be added in an amount necessary to inactivate the enzyme, but where reactivation is easily achieved by dilution of the inhibited enzyme/stabilizing agent complex in an aqueous medium. When the enzyme is in an inactive form, it is prevented from self-degradation and other spontaneous, chemically irreversible events. Examples of reversible inhibitors are aromatic acids and lower alkyl carboxylic acids such as propanoic and butyric acids. As used herein, the term "lower carboxylic acid" refers to a compound having a carboxylic acid group and from 2–4 carbon atoms in total. Preferred inhibitors include aromatic acid derivatives, such as benzoic acid. The preferred range of an aromatic acid derivative used in the present invention is 0.01 to 5.0% w/v.

Still other ingredients may optionally be added to the liquid enzyme compositions of the present invention. Such ingredients include buffering agents, such as, Tris or phosphate buffers; tonicity adjusting agents, such as NaCl or KCl, and pH adjusting agents such as sodium hydroxide, Tris, triethanolamine and hydrochloric acid.

The compositions may contain one or more surfactants selected from anionic, non-ionic or amphoteric classes. Examples of non-ionic surfactants include alkyl polyoxyethylene alcohols, alkyl phenyl polyoxyethylene alcohols, polyoxyethylene fatty acid esters, polyethylene oxide-polypropylene oxide copolymers such as polaxomers and polaxamines. Examples of anionic surfactants include alkyl sarcosinates and alkyl glutamates. Examples of amphoteric surfactants include alkyliminopropionates and alkylamphoacetates. In general, 0 to 5% w/v of the surfactant will be included in the compositions of the present invention.

The enzymes which may be utilized in the compositions and methods of the present invention include all enzymes which: (1) are useful in removing deposits from contact lenses; (2) cause, at most, only minor ocular irritation in the event a small amount of enzyme contacts the eye as a result of inadequate rinsing of a contact lens; (3) are relatively chemically stable and effective in the presence of the anti-microbial agents described below; and (4) do not adversely affect the physical or chemical properties of the lens being treated. The proteolytic enzymes used herein must have at least a partial capability to hydrolyze peptide-amide bonds in order to reduce the proteinaceous material found in lens deposits to smaller water-soluble subunits. Typically, such enzymes will exhibit some lipolytic, amylolytic or related activities associated with the proteolytic activity and may be neutral, acidic or alkaline. In addition, separate lipases or carbohydrases may be used in combination with the proteolytic enzymes. For purposes of the present specification, enzymes which satisfy the foregoing requirements are referred to as being "ophthalmically acceptable."

Examples of ophthalmically acceptable proteolytic enzymes which may be utilized in the present invention include but are not limited to pancreatin, trypsin, subtilisin, collagenase, keratinase, carboxypeptidase, papain, bromelain, aminopeptidase, elastase, Aspergillo peptidase, pronase E (from *S. griseus*), dispase (from *Bacillus polymyxa*) and mixtures thereof. If papain is used, a reducing agent, such as N-acetylcysteine, may be required.

Microbially derived enzymes, such as those derived from Bacillus, Streptomyces, and Aspergillus microorganisms, represent a preferred type of enzyme which may be utilized in the present invention. Of this sub-group of enzymes, the most preferred are the Bacillus derived alkaline proteases generically called "subtilisin" enzymes.

The identification, separation and purification of enzymes is known in the art. Many identification and isolation techniques exist in the general scientific literature for the isolation of enzymes, including those enzymes having proteolytic and mixed proteolytic/lipolytic/amylolytic activity. The enzymes contemplated by this invention can be readily obtained by known techniques from plant, animal or microbial sources.

With the advent of recombinant DNA techniques, it is anticipated that new sources and types of stable proteolytic enzymes will become available. Such enzymes should be considered to fall within the scope of this invention so long as they meet the criteria set forth herein.

Pancreatin, subtilisin and trypsin are preferred enzymes for use in the present invention. Pancreatin is extracted from mammalian pancreas, and is commercially available from various sources, including Scientific Protein Laboratories (Waunakee, Wis., U.S.A.), Novo Industries (Bagsvaerd, Denmark), Sigma Chemical Co. (St. Louis, Mo., U.S.A.), and Boehringer Mannheim (Indianapolis, Ind., U.S.A.). Pancreatin USP is a mixture of proteases, lipases and amylases, and is defined by the *United States Pharmacopeia* ("USP"). The most preferred form of pancreatin is Pancreatin 9X. As utilized herein, the term "Pancreatin 9X" means a filtered (0.2 microns) pancreatin containing nine times the USP protease unit content. Subtilisin is derived from Bacillus bacteria and is commercially available from various commercial sources including Novo Industries (Bagsvaerd, Denmark), Fluka Biochemika (Buchs, Switzerland) and Boehringer Mannheim (Indianapolis, Ind., U.S.A.).

Trypsin is a 23,800 dalton protease with 6 disulfide bridges. Trypsin can be synthesized or obtained from various sources, such as porcine, bovine or swine pancreatin. Trypsin is also available from commercial sources such as Sigma Chemical Co. (St. Louis, Mo.), Biofac Co. (United Kingdom) and Novo Nordisk (Denmark). Trypsin may vary from species to species, but in general will be highly homologous with porcine or human trypsin.

The most preferred enzymes of the present invention are the alkyl trypsins. It has been discovered that alkyl trypsins ("Al-trypsin(s)") are more stable in the liquid compositions than the native trypsin, or other native enzymes.

As used herein, "Al-trypsin" refers to a covalently modified trypsin wherein one or more of its lysine epsilon-amino groups has been mono-alkylated or di-alkylated to form the corresponding monoalkylamino or dialkylamino group. The alkyl group attached to the amine may be a primary or branched $C_{1-12}$ group. Preferred Al-trypsins of the present invention are those wherein the alkyl group is a primary or branched $C_{1-4}$ group. Alkylation of trypsin is generally performed by reductive alkylation. The degree of alkylation of the lysine epsilon-amino groups will depend on the reaction conditions of the reductive alkylation process. For example, if the reaction cycle is repeated a number of times and/or a higher reagent to enzyme ratio is used, then full alkylation, i.e., alkylation of all of the lysine epsilon-amino groups, will tend to be achieved. Al-trypsins of the present invention will preferably be fully dialkylyated at all of their lysine epsilon-amino groups. The most preferred Al-trypsin is methyl trypsin ("Me-trypsin"). The most preferred Me-trypsin of the present invention will be derived from porcine tissue sources and will be fully dimethylated, as described above.

Al-trypsin may be synthesized by the process of reductive alkylation of trypsin, as generally described in Scheme 1, below.

Other Al-trypsins may be prepared by methods analogous to Example 1, wherein formaldehyde is replaced by other alkylating reagents. For example, ethyl trypsin ("Et-trypsin") may be synthesized by an analogous method described in Example 1 and Scheme 1 above, wherein acetaldehyde is used as the alkylating reagent in place of formaldehyde.

The liquid enzyme compositions of the present invention will have an enzyme concentration sufficient to provide an effective amount of enzyme to remove substantially or to reduce significantly deposits of proteins, lipids, muco- Scheme 1

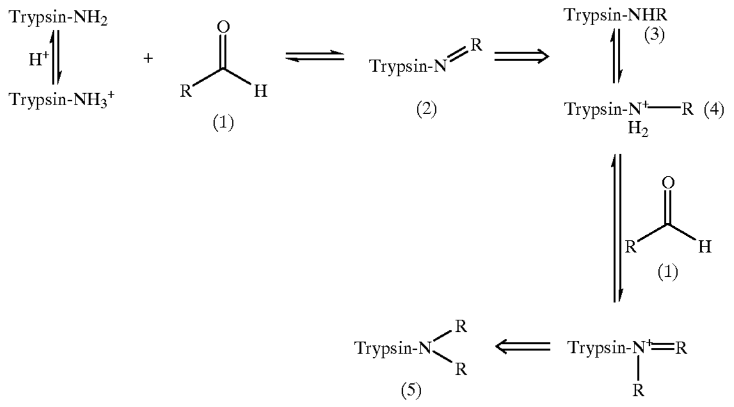

wherein, R is branched or unbranched $C_{1-12}$ alkyl.

As illustrated in scheme 1, the epsilon amino group of the lysine residues of trypsin is reacted with aldehydic alkylating reagent (1) to afford the alkylimino product (2). The alkylimino product (2) reduces to the resonant alkylamino species (3,4). The product (3,4) may react with another mole of the alkylating reagent (1) to yield the dialkylamino trypsin (5). As illustrated above, the resultant alkylated trypsin may either be mono or dialkylated at the lysine epsilon-amino groups.

EXAMPLE 1

Me-trypsin may be prepared by the following synthesis:

The following solutions are first prepared:

1. Borate buffer: 0.2 M sodium borate buffer, pH 9.2 containing 2 mg/ml benzamidine hydrochloride and a trace amount of n-octanol.

2. Trypsin: 1 g in 150 ml borate buffer.

To the 150 ml solution of trypsin, 10 ml of 1 M sodium borohydride is added followed quickly by 10 ml of 2.4 M formaldehyde. Three more volumes of sodium borohydride and formaldehyde are added at 10 minute intervals. The reaction solution is then acidified with glacial acetic acid to approximately pH 4.2 and then dialyzed extensively against 2 mM HCl at 4° C. (8 changes of 2 L each within 24 hours). The dialyzed solution is finally lyophylized for over 20 hours.

The above reactions are further described in Rice, R H, Means, G E and Brown, W D. *Stabilization of bovine trypsin by reductive methylation, Biochimica et Biophysica Acta,* volume 492, pages 316–321 (1977); and Means, G E and Feeney, R E. *Reductive alkylation of amino groups in proteins, Biochemistry,* volume 7, pages 2192–2210 (1968). Me-trypsin is also available from commercial sources such as Sigma Chemical Co. and Promega Corp. (Madison, Wis.).

polysaccharides and other materials typically found on human-worn contact lenses when a small amount of a composition is added to a diluent. As used herein, such a concentration is referred to as "an amount effective to clean the lens." The amount of enzyme used in the liquid enzyme compositions of the present invention will generally range from about 0.05 to 5% w/v. The selection of a specific concentration will depend on various factors, such as: the enzyme or combination of enzymes selected; the purity, specificity and efficacy of the enzyme(s) selected; the type of lenses to be cleaned; the intended frequency of cleaning (e.g., daily or weekly); and the intended duration of each cleaning.

During storage, some of the activity of the enzyme may be lost, depending on length of storage and temperature conditions. Thus, the liquid enzyme compositions of the present invention may be prepared with initial amounts of enzyme that exceed the concentration ranges described herein. The preferred compositions of the present invention will generally contain one or more enzymes in an amount of about 300–6000 PAU/mL. The compositions will most preferably contain about 900–3000 PAU/mL, which corresponds to pancreatin in the range of about 1 to 3% w/v; subtilisin in a range of about 0.1 to 0.5% w/v; trypsin in the range of about 0.1 to 0.5% w/v; and Me-trypsin in the range of about 0.1 to 0.5% w/v. For purposes of this specification, a "proteolytic activity unit" or "PAU" is defined as the amount of enzyme activity necessary to generate one microgram (mcg) of tyrosine per minute ("mcg Tyr/min"), as determined by the casein-digestion, colorimetric assay described below.

Casein-digestion assay

A 5.0 mL portion of casein substrate (0.65% casein w/v) is equilibrated for 10 minutes (min)±5 seconds (sec) at 37° C. A 1.0 mL portion of enzyme solution (0.2 mg/ml) is then added to the casein substrate and the mixture vortexed, then incubated for 10 min±5 sec at 37° C. After incubation, 5.0 mL of 14% trichloroacetic acid is added and the resultant mixture immediately vortexed. The mixture is incubated for at least another 30 min, then vortexed and centrifuged for 15–20 min (approx. 2000 rpm). The supernatant of the centrifuged sample is filtered into a serum filter sampler and a 2.0 mL aliquot removed. To the 2.0 mL sample is added 5.0 mL of 5.3% $Na_2CO_3$. The sample is vortexed, 1.0 mL of 0.67 N Folin's Phenol reagent is added, and the sample is immediately vortexed again, then incubated for 60 min at 37° C. The sample is then read on a visible light spectrophotometer at 660 nanometers versus purified water as the reference. The sample concentration is then determined by comparison to a tyrosine standard curve.

The cleaning obtained with the liquid enzyme compositions of the present invention is a function of the time. The soaking times utilized will generally vary from about 1 hour to overnight. However, if longer soaking periods (e.g., 24 hours) were to be employed, lower concentrations than those described above can be utilized.

The cleaning methods of the present invention involve the use of a small amount of the above-described liquid enzyme compositions to facilitate the removal of proteins and other deposits from contact lenses. The amount of enzyme composition utilized in particular embodiments of the present invention may vary, depending on various factors, such as the purity of the enzyme utilized, the proposed duration of exposure of lenses to the compositions, the nature of the lens care regimen (e.g., the frequency of lens disinfection and cleaning), the type of lens being treated, and the use of adjunctive cleaning agents (e.g., surfactants). However, the cleaning methods of the present invention will generally employ an amount of the above-described liquid enzyme compositions sufficient to provide a final enzyme concentration of about 1–100 PAU/mL, following dispersion of the liquid enzyme compositions in a disinfecting solution or other aqueous solvent. A final concentration of about 5–25 PAU/mL is preferred.

As indicated above, the liquid enzyme compositions of the present invention contain relatively minor amounts of ionic solutes. More specifically, the compositions do not contain bulking agents, effervescent agents or other ionic solutes commonly contained in prior enzyme tablets. The present compositions do contain the ionic solutes of borate or boric acid compounds and hydrochloric acid and/or sodium hydroxide, but the concentration of these solutes in the present compositions is relatively low. The compositions are therefore substantially nonionic. Moreover, as a result of the fact that the compositions are formulated as concentrated, multi-dose liquids, only a small amount of the compositions, generally one or two drops, is required to clean a contact lens. The present compositions therefore have very little impact on the ionic strength of disinfecting solutions. As explained below, this feature of the present invention is particularly important when the liquid enzyme compositions are combined with disinfecting solutions which contain ionic antimicrobial agents, such as polyquaternium-1.

The antimicrobial activity of disinfecting agents, particularly polymeric quaternary ammonium compounds such as polyquaternium-1, is adversely affected by high concentrations of sodium chloride or other ionic solutes. More specifically, polymeric quaternary ammonium compounds, and particularly those of Formula (I), below, lose antimicrobial activity when the concentration of ionic solutes in the disinfecting solution is increased. The use of solutions having low ionic strengths (i.e., low concentrations of ionic solutes such as sodium chloride) is therefore preferred. Since both ionic solutes (e.g., sodium chloride) and nonionic solutes (e.g., glycerol) affect the osmolality and tonicity of a solution, osmolality and tonicity are indirect measures of ionic strength. However, the low ionic strengths preferably utilized in the cleaning and disinfecting methods of the present invention generally correspond to tonicities/osmolalities in the range of hypotonic to isotonic, and more preferably in the range of 150 to 350 milliOsmoles per kilogram (mOs/kg). A range of 200 to 300 mOs/kg is particularly preferred, and an osmolality of about 220 mOs/kg is most preferred.

The liquid enzyme compositions of the present invention demonstrate effective cleaning efficacy while exhibiting minimal adverse effects or, more preferably, enhanced effects on the antimicrobial activity of disinfecting solutions.

The cleaning methods of the present invention utilize an aqueous solvent. The aqueous solvent may contain various salts such as sodium chloride and potassium chloride, buffering agents such as boric acid and sodium borate, and other agents such as chelating agents and preservatives. An example of a suitable aqueous solvent is a saline solution, such as Unisol® Plus Solution (registered trademark of Alcon Laboratories).

The cleaning and disinfecting methods of the present invention employ a disinfecting solution as the aqueous diluent for the dilution of a concentrated liquid enzyme composition of the present invention. The disinfecting solution will contain at least one anti-microbial agent, as discussed below. In general, the disinfecting solution may also contain sodium chloride and other excipients which together provide an ophthalmically compatible solution. As will be appreciated by those skilled in the art, the disinfecting solutions utilized in the present invention may contain various other components such as suitable buffering agents, chelating and/or sequestering agents and tonicity adjusting agents. The disinfecting compositions may also contain surfactants. In general, the disinfecting compositions will contain one or more anti-microbial agents (e.g., PHMB or polyquaternium-1), a buffer (e.g., borate), citrates, tonicity agents (e.g., NaCl, sugars), a chelating agent (e.g., EDTA), and surfactants (e.g., block copolymers). Other agents which enhance the anti-microbial efficacy of the compositions, such as amino alcohols and alkylamines, may also be added. Preferred disinfecting compositions comprise polyquatemium-1, sodium borate, boric acid, propylene glycol and Pluronic P-103. The most disinfecting compositions comprise boric acid, sorbitol, 95% 2-amino-2-methyl-1-propanol ("AMP-95"), sodium citrate, sodium chloride, disodium edetate, polyquaternium-1, poloxomine 1304 ("Tetronic 1304") and myristamidopropyl dimethyl amine ("MAPDA").

As stated above, the cleaning and disinfecting methods of the present invention utilize a disinfecting solution containing an antimicrobial agent. Antimicrobial agents can be oxidative, such as hydrogen peroxide, or non-oxidative polymeric antimicrobial agents which derive their antimicrobial activity through a chemical or physicochemical interaction with the organisms. As used in the present specification, the term "polymeric antimicrobial agent" refers to any nitrogen-containing polymer or co-polymer which has antimicrobial activity. Preferred polymeric antimicrobial agents include: polyquaternium-1, which is a polymeric quaternary ammonium compound; and polyhexamethylene biguanide ("PHMB") or polyaminopropyl biguanide ("PAPB"), which is a polymeric biguanide. These preferred antimicrobial agents are disclosed in U.S. Pat.

Nos. 4,407,791 and 4,525,346, issued to Stark, and 4,758,595 and 4,836,986, issued to Ogunbiyi, respectively. The entire contents of the foregoing publications are hereby incorporated in the present specification by reference. Other antimicrobial agents suitable in the methods of the present invention include: other quaternary ammonium compounds, such as benzalkonium halides, and other biguanides, such as chlorhexidine. The antimicrobial agents used herein are preferably employed in the absence of mercury-containing compounds such as thimerosal.

The most preferred antimicrobial agents are polymeric quaternary ammonium compounds of the structure:

(I)

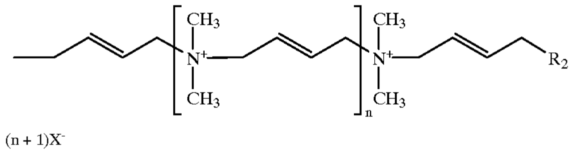

wherein:

$R_1$ and $R_2$ can be the same or different and are selected from:

$N^+(CH_2CH_2OH)_3X^-$, $N(CH_3)_2$ or OH;

$X^-$ is a pharmaceutically acceptable anion, preferably chloride; and n=integer from 1 to 50.

The most preferred compounds of this structure is polyquaternium-1, which is also known as Onamer M™ (registered trademark of Onyx Chemical Corporation) or as Polyquad® (registered trademark of Alcon Laboratories, Inc.). Polyquaternium-1 is a mixture of the above referenced compounds, wherein $X^-$ is chloride and $R_1$, $R_2$ and n are as defined above.

The above-described antimicrobial agents are utilized in the methods of the present invention in an amount effective to eliminate substantially or to reduce significantly the number of viable microorganisms found on contact lenses, in accordance with the requirements of governmental regulatory agencies, such as the United States Food and Drug Administration. For purposes of the present specification, that amount is referred to as being "an amount effective to disinfect" or "an antimicrobially effective amount." The amount of antimicrobial agent employed will vary, depending on factors such as the type of lens care regimen in which the method is being utilized. For example, the use of an efficacious daily cleaner in the lens care regimen may substantially reduce the amount of material deposited on the lenses, including microorganisms, and thereby lessen the amount of antimicrobial agent required to disinfect the lenses. The type of lens being treated (e.g., "hard" versus "soft" lenses) may also be a factor. In general, a concentration in the range of about 0.000001% to about 0.01% by weight of one or more of the above-described antimicrobial agents will be employed. The most preferred concentration of the polymeric quaternary ammonium compounds of Formula (I) is about 0.001% by weight.

Oxidative disinfecting agents may also be employed in the methods of the present invention. Such oxidative disinfecting agents include various peroxides which yield active oxygen in solution. Preferred methods will employ hydrogen peroxide in the range of 0.3 to 3.0% to disinfect the lens. Methods utilizing an oxidative disinfecting system are described in U.S. Pat. No. Re 32,672 (Huth, et al.), the entire contents of which are hereby incorporated in the present specification by reference.

The methods of the present invention will typically involve adding a small amount of a liquid enzyme composition of the present invention to about 2 to 10 mL of an aqueous solvent or disinfecting solution, placing the soiled lens into the enzyme/solvent or enzyme/disinfectant solution, and soaking the lens for a period of time effective to clean or clean and disinfect the lens. The amount of liquid enzyme composition utilized can vary based on factors such as the amount of aqueous solvent or disinfecting solution used, but generally it is about 1 to 2 drops. Preferred methods involve adding I drop (approximately 30 $\mu$L) to 5 mL of aqueous solvent or disinfecting solution. The soiled lens can be placed in the aqueous solvent or disinfecting solution either before or after the addition of the liquid enzyme composition. Optionally, the contact lenses are first rubbed with a non-enzymatic daily surfactant cleaner prior to immersion in the enzyme/solvent or enzyme/disinfectant solution. The lens will typically be soaked overnight, but shorter or longer durations are contemplated by the methods of the present invention. A soaking time of 4 to 8 hours is preferred. The methods of the present invention allow the above-described regimen to be performed once per week, but more preferably, every day.

The following examples are presented to illustrate further, various aspects of the present invention, but are not intended to limit the scope of the invention in any respect.

EXAMPLE 2

The most preferred liquid enzyme composition of the present invention, and a preferred disinfecting solution for use in combination with that composition, are described below:

A. Liquid Enzyme Composition

| Ingredient | Amount (w/v) |
|---|---|
| Methyl Trypsin | 3000 Units/mL |
| Sodium Borate | 1.5% |
| Calcium chloride | 0.25% |
| Glycerol | 25% |
| PEG 400 | 50% |
| Polyquaternium-1 | 0.003% |
| Purified water | QS |
| NaOH/HCl | QS to pH 6 to 8 |

The above formulation was prepared by first adding glycerol and PEG-400 to 40% of the batch of purified water while mixing. To this mixture, sodium borate, calcium chloride and polyquaternium-1 were added and allowed to dissolve. The pH was then adjusted to the desired pH range with sodium hydroxide. The enzyme was then added and the volume adjusted to 100% with purified water. The optimal pH of the above formulation is 6.5.

B. Disinfecting Solution

The following formulation represents a preferred disinfecting composition:

| Ingredient | Amount % (w/v) |
|---|---|
| Polyquaternium-1 | 0.001 |
| Boric acid | 0.6 |
| Sodium chloride | 0.1 |

-continued

| Ingredient | Amount % (w/v) |
|---|---|
| AMP-95 | 0.45 |
| MAPDA | 0.0005 |
| Sorbitol | 1.2 |
| Sodium citrate | 0.65 |
| Tetronic 1304 | 0.05 |
| Disodium Edetate | 0.05 |
| NaOH/HCl | To adjust pH 6.5 to 8.0 |
| Purified water | QS |

The ingredients are dissolved with 90% of the volume of purified water, the pH is adjusted, and the volume is then brought up to 100% volume. The composition is then sterile filtered using a 0.2 $\mu$m membrane filter.

Various volumes of the above enzyme and aqueous compositions may be employed together in order to prepare a cleaning and disinfecting composition. Preferred methods involve adding 1 drop of Example 2A to about 5 mL of Example 2B.

EXAMPLE 3

The following liquid enzyme compositions are preferred embodiments of the present invention:

A. Liquid Methyl Trypsin or Trypsin Composition:

| Ingredient | Amount % (w/v) |
|---|---|
| Trypsin or Methyl Trypsin | 3000 Units/mL |
| Sodium Borate | 1.5 |
| Calcium chloride | 0.25 |
| Glycerol | 25 |
| PEG 400 | 25 |
| Polyquaternium-1 | 0.003 |
| Purified water | QS |
| NaOH/HCl | QS to pH 6 to 8 |

B. Liquid Methyl Trypsin Composition:

| Ingredient | Amount % (w/v) |
|---|---|
| Methyl Trypsin | 3000 Units/mL |
| Sodium Borate | 1.5 |
| Calcium chloride | 0.25 |
| Glycerol | 25 |
| PEG 400 | 50 |
| Polyquaternium-1 | 0.003 |
| Purified water | QS |
| NaOH/HCl | QS to pH 6 to 8 |

C. Liquid Trypsin Composition:

| Ingredient | Amount % (w/v) |
|---|---|
| Trypsin | 3000 Units/mL |
| Sodium Borate | 1.5 |
| Calcium chloride | 0.25 |
| Propylene Glycol | 25 |
| PEG 400 | 50 |
| Polyquaternium-1 | 0.003 |
| Purified water | QS |
| NaOH/HCl | QS to pH 6 to 8 |

The above compositions may be prepared by a similar method to that described in Example 2A.

EXAMPLE 4

The following are examples of disinfecting compositions useful in the methods of the present invention:

A. Disinfecting Composition:

| Ingredient | Amount % (w/v) |
|---|---|
| Polyquaternium-1 | 0.001 + 10% excess |
| Sodium chloride | 0.48 |
| Disodium Edetate | 0.05 |
| Citric acid monohydrate | 0.021 |
| Sodium citrate dihydrate | 0.56 |
| NaOH/HCl | QS to pH 6–8 |
| Purified water | QS |

To prepare the above formulation, sodium citrate dihydrate, citric acid monohydrate, disodium edetate, sodium chloride and polyquaternium-1, in the relative concentrations indicated above, were mixed with purified water and the components allowed to dissolve by stirring with a mixer. Purified water was added to bring the solution to almost 100%. The pH was recorded at 6.3 and adjusted to 7.0 with NaOH. Purified water was added to bring the solution to 100%. The solution was stirred and a pH reading of 7.0 was taken. The solution was then filtered into sterile bottles and capped.

B. Disinfecting Composition

| Ingredient | Amount % (w/v) |
|---|---|
| Polyquaternium-1 | 0.0002 |
| Sodium borate | 0.25 |
| Propylene glycol | 1.0 |
| Pluronic P-103 | 0.1 |
| NaOH/HCl | To adjust pH to 6.5 to 8.0 |
| Purified water | QS |

C. Disinfecting Composition:

| Ingredient | Amount % (w/v) |
|---|---|
| PHMB | 0.0001 |
| Sodium phosphate | 0.28 |
| Potassium phosphate | 0.06 |
| Sodium chloride | 0.7 |
| Disodium edetate | 0.05 |
| NaOH/HCl | To adjust to pH 6.5 to 8.0 |
| Purified water | QS |

D. Disinfecting Composition:

| Ingredient | Amount % (w/v) |
|---|---|
| Polyquaternium-1 | 0.001 + 10% excess |
| Sodium chloride | 0.48 |
| Boric Acid | 0.225 |
| Sodium Borate | 0.08 |
| Mannitol | 0.64 |
| Pationic 138C | 0.005 |
| Tetronic 1304 | 0.25 |
| Disodium Edetate | 0.05 |
| Citric acid monohydrate | 0.016 |
| Sodium citrate dihydrate | 0.46 |
| NaOH/HCl | QS to pH 6.5–8 |
| Purified water | QS |

The Example 4B–D disinfecting compositions are prepared in a similar way as those of Example 4A.

Azocasein Method:

The following solutions are used in this assay:

1) Buffer solution: 0.05 M sodium phosphate buffer containing 0.9% sodium chloride, pH 7.6.

2) Substrate solution: 2 mg/ml azocasein in the buffer solution mentioned above.

The assay is initiated by mixing 1 ml of an appropriately diluted (such that the enzyme activity is in the range of standard curve) enzyme composition in phosphate buffer with 2 ml of azocasein substrate solution (2 mg/ml). After incubation at 37° C. for 20 minutes, the mixture is removed from the incubator and 1 ml of trichloroacetic acid (14% w/v) is added to stop the enzyme reaction. The mixture is vortexed well and allowed to stand at room temperature for 20 minutes. After centrifuging at 2500 rpm (with a Beckman GS-6R Centrifuge) for 15 minutes, the supernatant is filtered with a serum sampler. 2 ml of the clear yellow filtrate is then adjusted to a neutral pH with 2 mL of 0.5 N sodium hydroxide and the absorbance of 440 nm wavelength light is measured with a spectrophotometer. The amount of azocasein hydrolyzed is calculated based on a standard curve of known concentrations of azocasein solution developed under identical conditions. An enzyme activity unit ("AZ U") is defined as that amount of enzyme which hydrolyzes 1 $\mu$g of azocasein substrate/minute at 37° C.

EXAMPLE 5

A comparison of the enzyme stabilizing efficacy of a composition of the present invention (Composition 1) with other enzyme compositions (Compositions 2–3) was performed. The various compositions were incubated at storage temperatures of 40°, 45° and 50° C. At the appointed time, aliquots were tested for enzyme activity by the azocasein method described above. Activity levels were compared with initial levels and expressed as percent remaining activity. The results are presented in Table 1, below:

TABLE 1

| Comparison of the Stability of a Present Invention Composition with Other Compositions | | | |
|---|---|---|---|
| Composition | 1 | 2 | 3 |
| Trypsin | 3000 U/mL | 2210 U/mL | — |
| Pancreatin | — | — | 2210 U/mL |
| Sodium Borate (% w/v) | 1.5 | 7.62 | 7.62 |
| Calcium Chloride ·2 $H_2O$ (% w/v) | 0.25 | — | — |
| Glycerol (% w/v) | 25 | — | — |

TABLE 1-continued

| | | | |
|---|---|---|---|
| PEG 400 (% w/v) | 50 | — | — |
| Propylene Glycol (% w/v) | — | 50 | 50 |
| Polyquad ® (% w/v) | 0.003 | — | — |
| Purified Water | QS | QS | QS |
| Sodium hydroxide | QS pH 6.5 | QS pH 6.0 | QS pH 6.0 |

| Temperature | Time | % Activity Remaining | | |
|---|---|---|---|---|
| 50° C. | 1 week | 98.7 | 65.4 | 39.8 |
| | 2 weeks | 92.9 | 57.1 | 34.7 |
| | 4 weeks | 91.4 | 61.9 | 26.7 |
| | 8 weeks | 91.9 | — | — |
| | 13 weeks | 87.8 | — | — |
| 45° C. | 1 week | 100 | 67.2 | 41.2 |
| | 2 weeks | 97.1 | 63.0 | 38.1 |
| | 4 weeks | 97.1 | 42.0 | 30.5 |
| | 8 weeks | 95.3 | — | — |
| | 12 weeks | 91.9 | — | — |
| 40° C. | 1 week | 100 | 85.8 | 60.9 |
| | 2 weeks | 98.1 | 83.8 | 56.4 |
| | 4 weeks | 100 | 75.0 | 48.7 |
| | 8 weeks | 98.2 | 49.8 | — |
| | 12 weeks | 95.4 | — | — |

FIG. 1 illustrates the proteolytic stability of the three compositions, at 40° C. As shown above and in FIG. 1, the present invention composition (Composition 1) demonstrated superior protease stabilizing efficacy over other compositions.

EXAMPLE 6

The following example illustrates the stabilizing efficacy of liquid enzyme compositions of the present invention (compositions 5–9) versus a composition outside the present invention (composition 4). The various compositions were incubated at storage temperatures of 40°, 45° and 50° C. At the appointed time, aliquots were tested for enzyme activity by the azocasein method, Activity levels were compared with initial levels and expressed as percent remaining activity. The results are presented in Table 2, below:

TABLE 2

| | Comparison of the Stability of Present Invention Compositions with Other Compositions | | | | | |
|---|---|---|---|---|---|---|
| Ingredients | 4 | 5 | 6 | 7 | 8 | 9 |
| Methyl Trypsin | 3000 U/mL | 3000 U/mL | 3600 U/mL | 3600 U/mL | 3600 U/mL | 3600 U/mL |
| Sodium Borate (% w/v) | 1.5 | 1.5 | 1.5 | 1.5 | 1.5 | 1.5 |
| Calcium Chloride· 2 $H_2O$ (% w/v) | - 0 - | 0.25 | 0.25 | 0.25 | 0.5 | 0.25 |
| Glycerol (% w/v) | 35 | 35 | 35 | 35 | 35 | 25 |
| PEG 400 (% w/v) | 40 | 40 | 40 | 40 | 40 | 25 |

TABLE 2-continued

| pH | | 6.0 | 6.0 | 7.0 | 8.0 | 7.0 | 6.0 |
|---|---|---|---|---|---|---|---|
| Temp | Time | % Activity Remaining | | | | | |
| 50° C. | 2 weeks | 66.7 | 86.5 | 91.0 | 91.3 | 95.9 | 95.5 |
| 45° C. | 2 weeks | 78.0 | 80.7 | 89.7 | 92.0 | 97.3 | 98.1 |
| | 4 weeks | 37.11 | 55.0 | 72.0 | 82.1 | 74.9 | 86.0 |
| | 8 weeks | | | 72.3 | 88.1 | 85.3 | 98.0 |
| | 12 weeks | | | | 59.6 | 75.5 | 78.4 |
| 40° C. | 2 weeks | 84.7 | 97.4 | 101.4 | 98.0 | 96.8 | 96.2 |
| | 4 weeks | 70.7 | 94.7 | 85.9 | 98.8 | 84.5 | 90.0 |
| | 8 weeks | | 59.8 | 90.2 | 98.8 | 87.9 | 100.0 |
| | 12 weeks | | | 69.3 | 73.6 | 92.7 | 96.3 |

The data of Table 2 demonstrate the stabilizing efficacy of various liquid enzyme compositions of the present invention.

EXAMPLE 7

The following example illustrates the stabilizing efficacy of liquid enzyme compositions of the present invention. The various compositions were incubated at storage temperatures of 45° and 50° C. At the appointed time, aliquots were tested for enzyme activity by the azocasein method. Activity levels were compared with initial levels and expressed as percent remaining activity. The results are presented in Table 2, below:

disinfecting solution of Example 2B, followed by the addition of 2 drops of the liquid enzyme composition of Example 2A. A similarly inoculated 10 mL volume of the disinfecting solution of Example 2B was used as a control. The solutions were maintained at room temperature throughout the test. Each microorganism and test solution was tested individually. Sets of four replicate (n=8) samples were tested for each organism.

At selected time intervals of 1, 2, 3, 4, 6, 24 and 168 hours, a I mL volume of the inoculated test solution containing *Serratia marcescens, Staphylococcus aureus,*

TABLE 3

| Ingredients | 10 | 11 | 12 | 13 | 14 | 15 |
|---|---|---|---|---|---|---|
| | Stability of a Liquid Enzyme Composition of the Present Invention | | | | | |
| Methyl Trypsin | 3600 U/mL | 3600 U/mL | 3600 U/mL | 3600 U/mL | 3600 U/mL | 3600 U/mL |
| Sodium Borate (% w/v) | 1.5 | 1.5 | 1.5 | 1.5 | 1.5 | 1.5 |
| Calcium Chloride· 2 $H_2O$ (% w/v) | 0.25 | 0.25 | 0.5 | 0.25 | 0.25 | 0.25 |
| Glycerol (% w/v) | 35 | 35 | 35 | 25 | 25 | 25 |
| PEG 400 (% w/v) | 40 | 40 | 40 | 25 | 25 | 25 |
| pH | 7.5 | 8.0 | 8.0 | 6.0 | 6.5 | 7.0 |

| Temp | Time | % Activity Remaining | | | | | |
|---|---|---|---|---|---|---|---|
| 50° C. | 2 weeks | 84.9 | 86.8 | 84.4 | 90.5 | 84.5 | 89.2 |
| | 4 weeks | 86.7 | 81.4 | 77.8 | 90.5 | 90.7 | 89.0 |
| | 8 weeks | 84.5 | 76.2 | 70.1 | 88.7 | 87.4 | 81.6 |
| | 12 weeks | 81.4 | — | — | 82.5 | 81.9 | 81.5 |
| 45° C. | 2 weeks | 94.6 | 91.2 | 88.5 | 96.6 | 92.1 | 92.3 |
| | 4 weeks | 88.3 | 83.9 | 81.3 | 94.6 | 92.7 | 91.2 |
| | 8 weeks | 86.4 | 80.3 | 77.1 | 92.7 | 88.7 | 87.2 |
| | 12 weeks | 85.6 | 76.1 | — | 86.0 | 86.4 | 86.3 |

EXAMPLE 8

The disinfecting efficacy of the cleaning and disinfecting methods of the present invention was evaluated by determining the rate and extent of kill achieved with a cleaning and disinfecting solution comprised of the Example 2A (trypsin) and 2B compositions. The multi-purpose solution was tested against *Serratia marcescens, Staphylococcus aureus, Pseudomonas aeruginosa, Candida albicans* and *Fusarium solani*. The test procedures and results are described below.

The following procedure was used:

A 0.1 mL volume of inoculum ($10^8$ colony forming units/mL) was first added to a 10 mL volume of the Pseudomonas aeruginosa, Candida albicans and *Fusarium solani* was removed and appropriate serial dilutions were made in sterile 0.9% sodium chloride solution dilution blanks. Pour-plates were prepared with soybean-casein digest agar containing 0.07% Asolectin and 0.5% Polysorbate 80. At Time 0, a 1.0 mL volume of the saline control was removed and serial dilution pour-plates were prepared using the same recovery medium and dilution blanks. The Time 0 saline control count was used as the initial count. The pour-plates were incubated at 30°–35° C. for appropriate incubation periods. The number of surviving organisms at each time interval was then determined. The test results, expressed as log reductions are presented in Table 6 below.

TABLE 6

Disinfecting Efficacy of a Cleaning and Disinfecting Solution of the Present Invention

| Microorganism | Time (hours) | Log Reduction |
|---|---|---|
| *C. albicans* | 1 | 1.2 |
| | 2 | 1.7 |
| | 3 | 1.9 |
| | 4 | 2.2 |
| | 6 | 3.0 |
| | 24 | 5.9* |
| | 168 | 5.9* |
| *F. solani* | 1 | 3.5 |
| | 2 | 4.2 |
| | 3 | 4.4 |
| | 4 | 4.5 |
| | 6 | 5.3 |
| | 24 | 5.8* |
| | 168 | 5.8* |
| *P. aeruginosa* | 1 | 6.0* |
| | 2 | 6.0* |
| | 3 | 6.0* |
| | 4 | 6.0* |
| | 6 | 6.0* |
| | 24 | 6.0* |
| | 168 | 6.0* |
| *S. marcescens* | 1 | 3.1 |
| | 2 | 3.7* |
| | 3 | 4.1 |
| | 4 | — |
| | 6 | 4.8 |
| | 24 | 6.1* |
| | 168 | 6.1* |
| *S. aureus* | 1 | 2.9 |
| | 2 | 3.2 |
| | 3 | 3.4 |
| | 4 | 3.6 |
| | 6 | 3.3 |
| | 24 | 3.8 |
| | 168 | 6.1* |

*Indicates that no survivors (less than 10 cfu/mL) were recovered

The invention in its broader aspects is not limited to the specific details shown and described above. Departures may be made from such details within the scope of the accompanying claims without departing from the principles of the invention and without sacrificing its advantages.

What is claimed is:

1. A stable liquid enzyme composition for cleaning a contact lens comprising: a proteolytic enzyme in an amount effective to clean the lens; 40–85% w/v of a mixture of monomeric polyols and polyalkoxylated glycols, the glycols having molecular weights of from 200–600 daltons; an amount of a borate/boric acid compound effective to enhance the proteolytic stability of the enzyme; an amount of calcium ion effective to enhance the proteolytic stability of the enzyme; and water.

2. A composition according to claim 1, wherein the enzyme is selected from the group consisting of pancreatin, subtilisin, trypsin and methyl trypsin.

3. A composition according to claim 1, wherein the monomeric polyols are comprised of a 2–3 carbon polyol and the polyalkoxylated glycols are comprised of polyethylene glycols.

4. A composition according to claim 1, wherein the composition contains sodium borate in the amount of 1.5% w/v.

5. A composition according to claim 1, wherein the enzyme is selected from the group consisting of pancreatin, subtilisin, trypsin and methyl trypsin; the monomeric polyols and polyalkoxylated glycols are selected from the group consisting of glycerol, 1,2-propane diol, 1,3-propane diol, ethylene glycol, PEG-200, and PEG-400; the borate/boric acid compound is sodium borate in the amount of 1.5% w/v; and the composition contains 0.25% w/v of calcium chloride.

6. A composition according to claim 1, wherein the concentration of the enzyme is 0.05 to 5.0% w/v.

7. A composition according to claim 1, wherein the composition comprises 25% glycerol w/v, 50% PEG-400 w/v, 1.5% w/v sodium borate, 0.25% w/v calcium chloride and water.

8. A composition according to claim 7, wherein the enzyme is selected from the group consisting of pancreatin, subtilisin, trypsin and methyl trypsin.

9. A composition according to claim 7, wherein the enzyme is trypsin in the amount of at least 900 PAU/mL.

10. A composition according to claim 7, wherein the enzyme is methyl trypsin in the amount of at least 900 PAU/mL.

11. A method according to claim 1, wherein the enzyme is an Al-trypsin.

12. A method for cleaning and disinfecting a contact lens comprising:

placing the lens in an aqueous disinfecting solution containing an amount of an antimicrobial agent effective to disinfect the lens;

forming an aqueous disinfectant/enzyme solution by dispersing an amount of a liquid enzyme cleaning composition in said disinfecting solution, said cleaning composition comprising: a proteolytic enzyme in an amount effective to clean the lens; 40–85% w/v of a mixture of monomeric polyols and polyalkoxylated glycols, the glycols having a molecular weight of from 200–600 daltons; an amount of a borate/boric acid compound effective to enhance the proteolytic stability of the enzyme; an amount of calcium ion effective to enhance the proteolytic stability of the enzyme; and water; and soaking the lens in said aqueous disinfectant/enzyme solution for a period of time sufficient to clean and disinfect the lens.

13. A method according to claim 12, wherein the liquid enzyme cleaning composition comprises sodium borate in the amount of 1.5% w/v and calcium chloride in the amount of 0.25% w/v.

14. A method according to claim 12, wherein the monomeric polyols and polyalkoxylated glycols are comprised of 2–3 carbon polyols and polyethylene glycols.

15. A method according to claim 12, wherein the enzyme is selected from the group consisting of pancreatin, subtilisin, trypsin and methyl trypsin.

16. A method according to claim 12 wherein the enzyme is selected from the group consisting of pancreatin, subtilisin, trypsin and methyl trypsin; the monomeric polyols and polyalkoxylated glycols are selected from the group consisting of glycerol, 1,2-propane diol, 1,3-propane diol, ethylene glycol, PEG-200, and PEG-400; the borate/boric acid compound is sodium borate in the amount of 1.5% w/v; and the composition contains 0.25% w/v of calcium chloride.

17. A method according to claim 16, wherein the antimicrobial agent comprises 0.00001% to 0.05% w/v of polyquaternium-1.

18. A method according to claim 16, wherein the disinfecting solution comprises:

about 0.001% w/v of polyquaternium-1;

about 0.6% w/v of boric acid;

about 1.2% w/v of sorbitol;

about 0.65% w/v of sodium citrate;

about 0.1% w/v of sodium chloride;

about 0.05% w/v of poloxamine 1304;

about 0.05% w/v of disodium edetate;

about 0.45% w/v of 95% 2-amino-2methyl-1-propanol, about 0.0005% w/v of myristamidopropyl dimethyl amine; and water.

19. A method according to claim 12, wherein the concentration of the enzyme is 0.05 to 5.0% w/v.

20. A method according to claim 12, wherein the liquid enzyme cleaning composition comprises an enzyme, 25% glycerol w/v, 50% PEG-400 w/v, 1.5% w/v sodium borate, 0.25% w/v calcium chloride and water.

21. A method according to claim 20, wherein the enzyme is selected from the group consisting of pancreatin, subtilisin, trypsin and methyl trypsin.

22. A method according to claim 20, wherein the enzyme is trypsin in the amount of at least 900 PAU/mL.

23. A method according to claim 20, wherein the enzyme is methyl trypsin in the amount of at least 900 PAU/mL.

24. A method according to claim 20, wherein the antimicrobial agent comprises 0.00001% to 0.05% w/v of polyquaternium-1.

25. A method according to claim 12, wherein the antimicrobial agent comprises 0.00001% to 0.05% w/v of polyquaternium-1.

26. A method according to claim 12, wherein the disinfectant/enzyme solution has an osmolality of from 150 to 350 mOsmoles/kg.

27. A method according to claim 12, wherein the enzyme is an Al-trypsin.

28. A method of cleaning a contact lens which comprises:

forming an aqueous enzymatic cleaning solution by dispersing an amount of a liquid enzyme composition in an aqueous solvent, said liquid enzyme composition comprising a proteolytic enzyme in an amount effective to clean the lens; 40–85% w/v of monomeric polyols and polyalkoxylated glycols, the glycols having a molecular weight between 200–600 daltons; an amount of a borate/boric acid compound effective to enhance the proteolytic stability of the enzyme; an amount of calcium ion effective to enhance the proteolytic stability of the enzyme; and water; and soaking the lens in the enzymatic cleaning solution for a period of time sufficient to clean the lens.

29. A method according to claim 28, wherein the enzyme is selected from the group consisting of pancreatin, subtilisin, trypsin and methyl trypsin.

30. A method according to claim 28, wherein the monomeric polyols and polyalkoxylated glycols are comprised of 2–3 carbon polyols and polyethylene glycols.

31. A method according to claim 28, wherein the liquid enzyme cleaning composition comprises sodium borate in the amount of 1.5% w/v and calcium chloride in the amount of 0.25% w/v.

32. A method according to claim 28, wherein the enzyme is selected from the group consisting of pancreatin, subtilisin, trypsin and methyl trypsin; the monomeric polyols and polyalkoxylated glycols are selected from the group consisting of glycerol, 1,2-propane diol, 1,3-propane diol, ethylene glycol, PEG-200, and PEG-400; the borate compound is sodium borate in the amount of 1.5% w/v; and the composition contains 0.25% w/v of calcium chloride.

33. A method according to claim 28, wherein the concentration of the enzyme is 0.05 to 5.0% w/v.

34. A method according to claim 28, wherein the liquid enzyme cleaning composition comprises an enzyme, 25% glycerol w/v, 50% PEG-400 w/v, 1.5% w/v sodium borate, 0.25% w/v calcium chloride and water.

35. A method according to claim 34, wherein the enzyme is selected from the group consisting of pancreatin, subtilisin, trypsin and methyl trypsin.

36. A method according to claim 34, wherein the enzyme is trypsin in the amount of at least 900 PAU/mL.

37. A method according to claim 34, wherein the enzyme is methyl trypsin in the amount of at least 900 PAU/mL.

38. A method according to claim 28, wherein the enzyme is an Al-trypsin.

* * * * *